(12) United States Patent
Schmidt

(10) Patent No.: US 9,610,136 B2
(45) Date of Patent: Apr. 4, 2017

(54) DEVICE FOR THE CONTROLLED SUPPLY OF COMPRESSED AIR TO AT LEAST ONE PNEUMATICALLY OPERATED DENTAL INSTRUMENT

(71) Applicant: MEDTRONIC medizinisch-elekronische Gerategesellschaft mbH, Usingen (DE)

(72) Inventor: Alfred Schmidt, Usingen (DE)

( * ) Notice: Subject to any disclaimer, the term of this patent is extended or adjusted under 35 U.S.C. 154(b) by 133 days.

(21) Appl. No.: 14/086,220

(22) Filed: Nov. 21, 2013

(65) Prior Publication Data

US 2014/0178833 A1 Jun. 26, 2014

(51) Int. Cl.
  *A61C 1/00* (2006.01)
  *A61C 1/05* (2006.01)
(52) U.S. Cl.
  CPC ............ *A61C 1/0038* (2013.01); *A61C 1/052* (2013.01)
(58) Field of Classification Search
  CPC .................................................. A61C 1/0038
  See application file for complete search history.

(56) References Cited

U.S. PATENT DOCUMENTS

| | | | | |
|---|---|---|---|---|
| 3,924,660 A | * | 12/1975 | Woodhams | A61C 1/0038 137/637.1 |
| 4,069,587 A | * | 1/1978 | Peralta | A61C 1/0038 433/28 |
| 4,145,813 A | * | 3/1979 | Hall | A61C 1/0038 137/625.18 |
| 4,151,647 A | * | 5/1979 | Saupe | A61C 1/0038 433/28 |
| 4,188,976 A | * | 2/1980 | Austin, Jr. | A61C 1/0061 137/596.14 |
| 4,194,289 A | * | 3/1980 | Neri | A61C 1/0038 433/101 |
| 4,230,143 A | * | 10/1980 | Dettmann | A61C 1/0038 137/270 |

(Continued)

FOREIGN PATENT DOCUMENTS

| | | |
|---|---|---|
| DE | 10135555 | 2/2003 |
| DE | 102007013777 | 7/2008 |
| EP | 1236938 | 9/2002 |

*Primary Examiner* — Ralph Lewis
(74) *Attorney, Agent, or Firm* — Welsh Flaxman & Gitler LLC

(57) ABSTRACT

The invention relates to a device for the controlled supply of compressed air to at least one pneumatically operated dental instrument (5, 5', 5", 5''') from a supply and control unit (2), in which a dental instrument (5, 5', 5", 5''') is connected by a supply hose (4, 4', 4", 4''') for supplying compressed air with a valve mechanism (6) provided in the supply and control unit (2), the valve mechanism (6) having a plurality of pneumatic sliding valve units (9, 9', 9", 9'''). The pneumatic sliding valve units (9, 9', 9", 9''') of the valve mechanism (6) are accommodated in at least one valve body (10) and the valve body (10) has a plurality of control connections (12, 12', 12", 12'''), whereby each pneumatic sliding valve unit (9, 9', 9", 9''') corresponds to a control input (12, 12', 12", 12''') and pressurization of a control input (12, 12', 12", 12''') with switching compressed air opens the corresponding sliding valve unit (9") and locks the additional, closed sliding valve units (9, 9', 9''').

12 Claims, 11 Drawing Sheets

(56) References Cited

U.S. PATENT DOCUMENTS

| | | | | |
|---|---|---|---|---|
| 4,382,786 A | * | 5/1983 | Lohn | A61C 1/0038 433/100 |
| 4,944,676 A | * | 7/1990 | Hu | A61C 1/0061 433/100 |
| 5,201,899 A | * | 4/1993 | Austin, Jr. | A61C 1/0038 433/92 |

* cited by examiner

DEVICE FOR THE CONTROLLED SUPPLY OF COMPRESSED AIR TO AT LEAST ONE PNEUMATICALLY OPERATED DENTAL INSTRUMENT

BACKGROUND OF THE INVENTION

The invention relates to an apparatus for the controlled supply of compressed air to at least one pneumatically operated dental instrument from a supply and control unit. The dental instrument is connected to the supply and control unit by a supply hose for supplying compressed air under the control of a valve mechanism provided in the supply and control unit.

Pneumatically operated dental instruments are connected via a supply hose to a supply and control unit. A dental instrument normally consists of a handpiece element and a treatment implement held therein, for example, in the form of a drill or a similar implement. Pneumatically operated dental instruments usually comprise, in their respective handpiece element, at least one pneumatically operated motor unit, which is connected by a supply hose with the supply and control unit with the working medium, usually compressed air which is required for operation.

Normally, a plurality of pneumatically operated dental instruments are connected to a supply and control unit and are supplied, respectively, via a corresponding supply hose with the suitable working medium, usually compressed air. In this respect, it is desirable to supply the compressed air required for operation of the dental instrument exactly when it is needed for operation of the dental instrument. Also, pneumatically operated supply and control units, by which a plurality of dental instruments having different functions can be operated, have complex pneumatic controllers and corresponding wiring and they have single valve and switch devices, which under some circumstances can also be supplemented by electronic control components. Especially important in this respect is the proper operation of the supply and control unit, as well as the connected dental instruments. In particular, it is desirable that only the dental instrument currently in use is ready for operation and the remaining dental instruments held in the supply and control unit by corresponding holders on the supply and control unit are switched off.

It is an object of the present invention to provide a device for the controlled supply of compressed air to at least one pneumatically operated dental instrument, which enables the controlled supply of compressed air to exactly control one dental instrument while simultaneously switching off the additional dental instruments. The invention features a reliable functional principle and the device can be serviced quickly and easily. This object is achieved by a device for the controlled supply of compressed air to at least one pneumatically operated dental instrument from a supply and control unit, in which a dental instrument is connected by a supply hose for supplying compressed air with a valve mechanism provided in the supply and control unit.

SUMMARY OF THE INVENTION

It is an essential aspect of the device, according to the invention, that the pneumatic sliding valve units of the valve mechanism are accommodated in at least one valve body, the valve body comprises a plurality of control connections and each pneumatically switchable sliding valve unit corresponds to one control input, whereby the pressurization of a control input with switching compressed air opens the corresponding sliding valve unit and closes the other sliding valve units. This device results in the reliable controlled supply of the compressed air required for operation of a dental instrument with the simultaneous locking of the additional dental instruments, which insures that exactly one dental instrument is ready for operation. Also, the integration of the pneumatically switchable sliding valve units in a valve body with a one-piece design allows for easy and fast maintenance of the valve mechanism. Alternatively, the valve body can have a modular design, i.e. consisting of a plurality of valve body modules, which can be assembled by plug-type connections to constitute one common valve body system. This eliminates the complicated and often error-prone wiring of a plurality of valve units of the prior art.

It is also advantageous that the one sliding valve unit comprises one profiled sliding valve piston guided in one corresponding valve bore of the valve body. The valve body has a one-piece or modular design and the valve bores extend from the top side of the valve body along the valve body module to its bottom side. The monolithic or modular design of the valve body allows the cost-effective and fast manufacture of the valve mechanism, as well as its fast and easy expansion.

According to one further embodiment of the invention, a sliding valve unit comprises, in addition to the control input, at least one switch output, whereby the sliding valve units can be switched individually by pressurization of the respective corresponding control input with compressed air, due to axial displacement of the sliding valve piston in the valve bore along the longitudinal axis of the valve body.

The valve body comprises one upper and lower valve body half or valve body module half, whereby the valve bores are connected with each other by one first connection bore and first valve bore sections of the upper valve body half and one second connection bore and valve bore sections in the lower valve body half and the first and second connection bore in the valve body extend perpendicular to the valve bores. The second connection bore is provided for the supply of continuous compressed air to the valve bores.

According to an alternative embodiment of the invention, a valve bore comprises at least one first and second valve bore section with different bore diameters, whereby the profiling of the sliding valve piston is adapted to this course or direction of the bore cross section of the valve bores. The sliding valve pistons comprise one first and second piston section having a plurality of section-wise different piston diameters as well as a plurality of circumferential grooves. The first piston section is provided with at least one first and second circumferential groove and the second piston section is provided with one fourth and fifth circumferential groove, and connected with a central circumferential groove, which are constructed for holding respectively one sealing ring, especially one sealing O-ring.

The second piston section is provided with one first and second piston bore, which extend perpendicular to each other and constitute a part of a valve path. The valve bores and the sliding valve pistons are identical to each other.

For fastening of the dental instrument on the supply and control unit, a plurality of holder elements are provided, whereby one dental instrument corresponds exactly to one holder element. In this respect, one holder element corresponds to one switch element, which can be actuated by insertion of the dental instrument into the holder element or removal of the dental instrument from the holder element. The switch elements are provided for controlling the pressurization of the control inputs with switching compressed air.

Further, the present invention is directed to a valve mechanism having a plurality of pneumatic sliding valve units, in which the pneumatic sliding valve units of the valve mechanism are accommodated in a common valve body, in which the valve body comprises a plurality of control connections, and each pneumatic sliding valve unit corresponds to a control input, whereby pressurization of a control input with switching compressed air opens the corresponding sliding valve unit and locks the additional, closed sliding valve units.

DETAILED DESCRIPTION OF THE INVENTION

Figure 1:
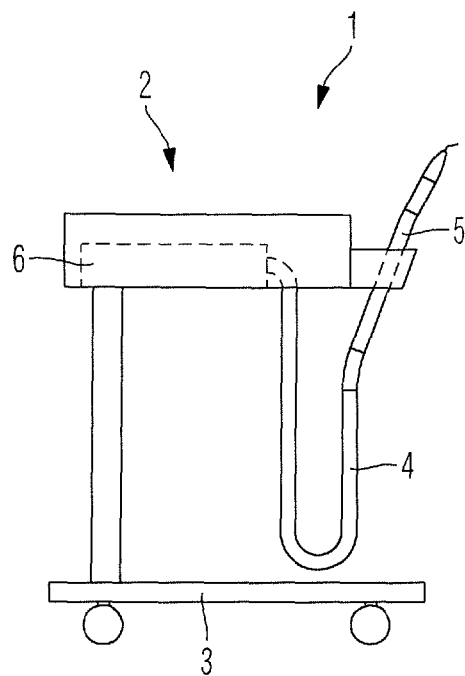
FIG. 1 shows a schematic side view of a dental instrument having a supply and control unit.

FIG. 1 depicts an exemplarily a dental device 1, which includes at least one supply and control unit 2. The supply and control unit 2 is designed for the controlled supply of a working media, preferably compressed air, as well as electrical power or control signals to at least one pneumatically operated dental instrument 5, 5', 5", 5'".

A dental device 1 includes, if desired, a wheeled cart 3, on which the supply and control unit 2 is provided. Alternatively, the dental device 1 can be part of a dental treatment unit, which is provided, in a rotatable and/or height adjustable manner on a treatment chair unit (not depicted in the figures).

A dental instrument 5, 5', 5", 5'" is connected to the supply and control unit 2 by a supply hose 4, 4', 4", 4'", whereby the supply hose 4, 4', 4", 4'" is connected directly or indirectly, by additional coupling elements (not depicted in the figures) with a valve mechanism 6 accommodated in the supply and control unit 2.

Starting from the valve mechanism 6, a transmission connection is established by the supply hose 4, 4', 4", 4'" for transmission of the working media, especially compressed air, to the pneumatically operated dental instrument 5, 5', 5", 5'". Preferably, one dental device 1 comprises a plurality of dental instruments 5, 5', 5", 5'", which are connected by a supply hose 4, 4', 4", 4'" with the valve mechanism 6 of the supply and control unit 2.

Figure 2:
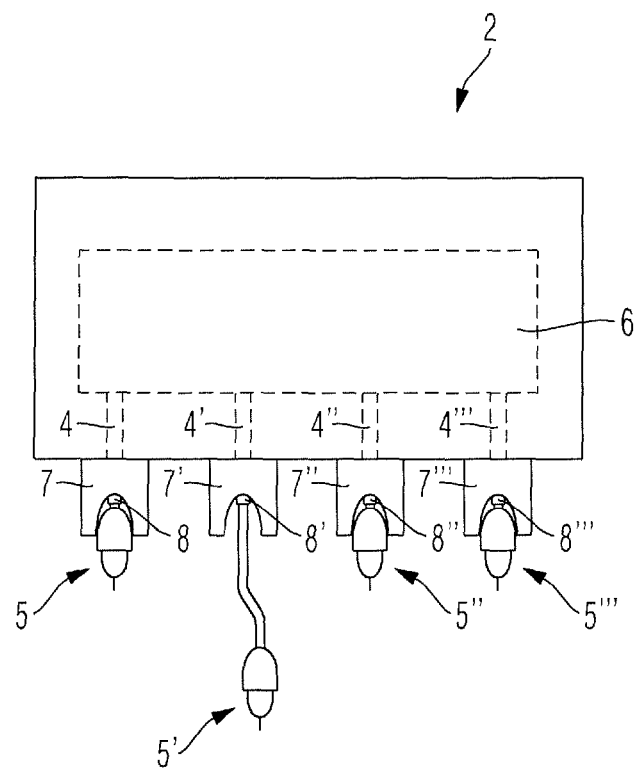
FIG. 2 shows a top view of a dental instrument having a supply and control unit according to FIG. 1.

FIG. 2, for the purpose of illustrating the fundamental design of such a dental device 1, depicts a first to a fourth dental instrument 5, 5', 5", 5'", which are respectively connected by a first to a fourth supply hose 4, 4', 4", 4'" with the supply and control unit 2. The number of dental instruments 5, 5', 5", 5'" connected to the dental device 1 is by no means limited to four, but can vary from two to ten dental instruments 5, 5', 5", 5'" without departing from the inventive idea.

A dental instrument 5, 5', 5", 5'" is understood to be a dental treatment instrument, for example a hand-held unit with an exchangeable treatment implement. The operation of such dental instrument 5, 5', 5", 5'" takes place via the aforementioned working media. In the case according to the invention, operation of the pneumatically operated dental instrument 5, 5', 5", 5'" requires the controlled supply of compressed air for driving the respective motor unit. The compressed air is supplied by the respective corresponding supply hose 4, 4', 4", 4'". It is also possible to transmit additional fluids such as water, blast air or electric power, and/or pneumatic and/or electric control signals by the supply hose 4, 4', 4", 4'".

For fastening the dental instrument 5, 5', 5", 5'" on the supply and control unit 2, a plurality of holder elements 7, 7', 7", 7'" are provided, whereby one dental instrument 5, 5', 5", 5'" corresponds respectively to exactly one holder element 7, 7', 7", 7'". The present embodiment provides for first to fourth holder elements 7, 7', 7", 7'", which are arranged next to each other and at a distance from each other and protrude from the front face of the supply and control unit 2 in the direction of the user. This allows the user easier and more direct access to the dental instruments 5, 5', 5", 5'" accommodated in the holder elements 7, 7', 7", 7'".

For holding of the dental instruments 5, 5', 5", 5'", the holder elements 7, 7', 7", 7'" comprise a recess having an at least partially U-shaped or arc-shaped cross section, into which the dental instruments 5, 5', 5", 5'" can be inserted from above. This makes it possible to establish a clamped and/or plug-type connection at least between the hand-held unit of a dental instrument 5, 5', 5", 5'" and the respective holder element 7, 7', 7", 7'". In particular, the dental instruments 5, 5', 5", 5'" are enclosed at least partially by the respective holder element 7, 7', 7", 7'" in their end section of the hand-held unit oriented toward the supply hose 4, 4', 4", 4'".

Further, in a preferred alternative embodiment, the holder elements 7, 7', 7", 7'" comprise a switch element 8, 8', 8", 8'", which is actuated accordingly upon insertion and/or removal of the dental instrument 5, 5', 5", 5'". This makes it possible to generate a pneumatic switching signal, by which actuation of the valve mechanism 6 could take place. The switch elements 8, 8', 8", 8'" are preferably provided in the section-wise U-shaped or arc-shaped recess of the holder element 7, 7', 7", 7'".

Figure 3:
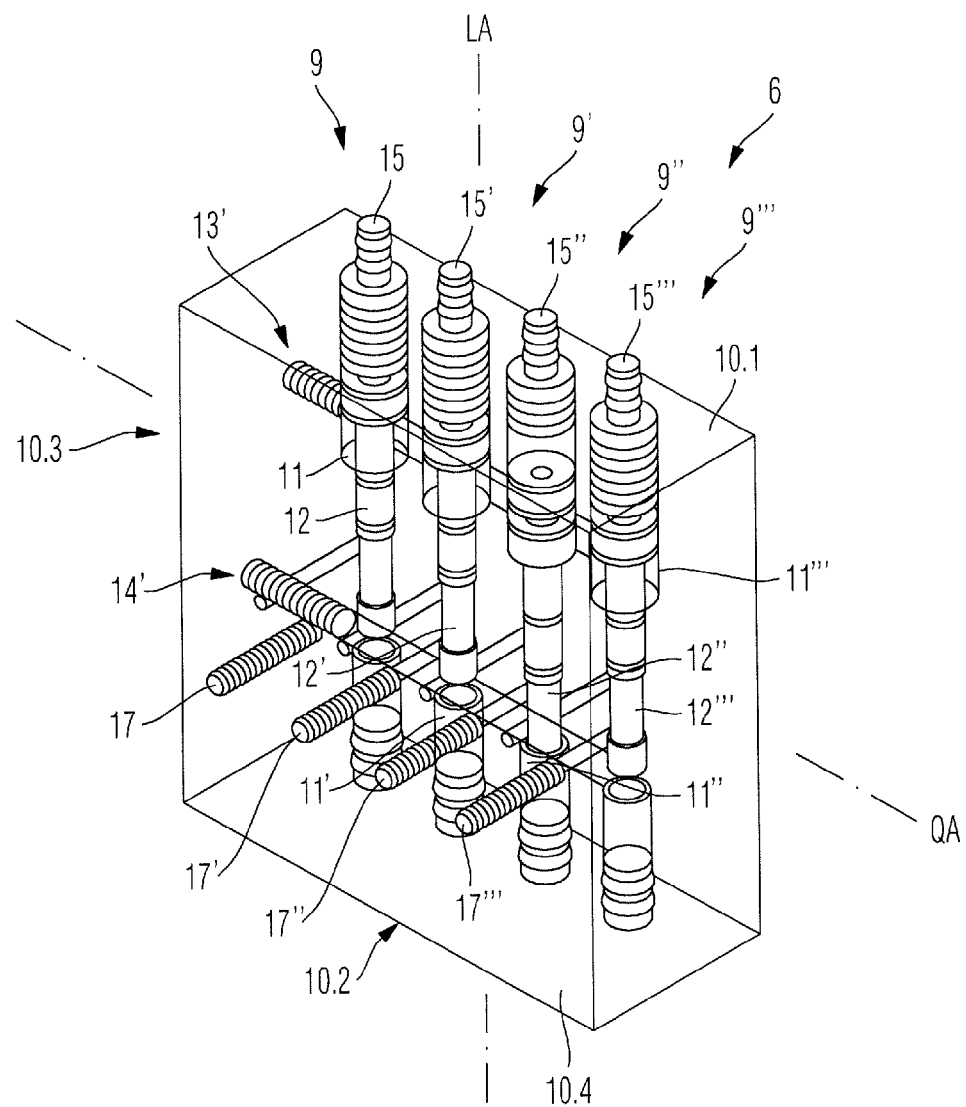
FIG. 3 shows a perspective view of a valve mechanism according to the invention that is integrated in the supply and control unit of FIGS. 1 and 2.
Figure 4:
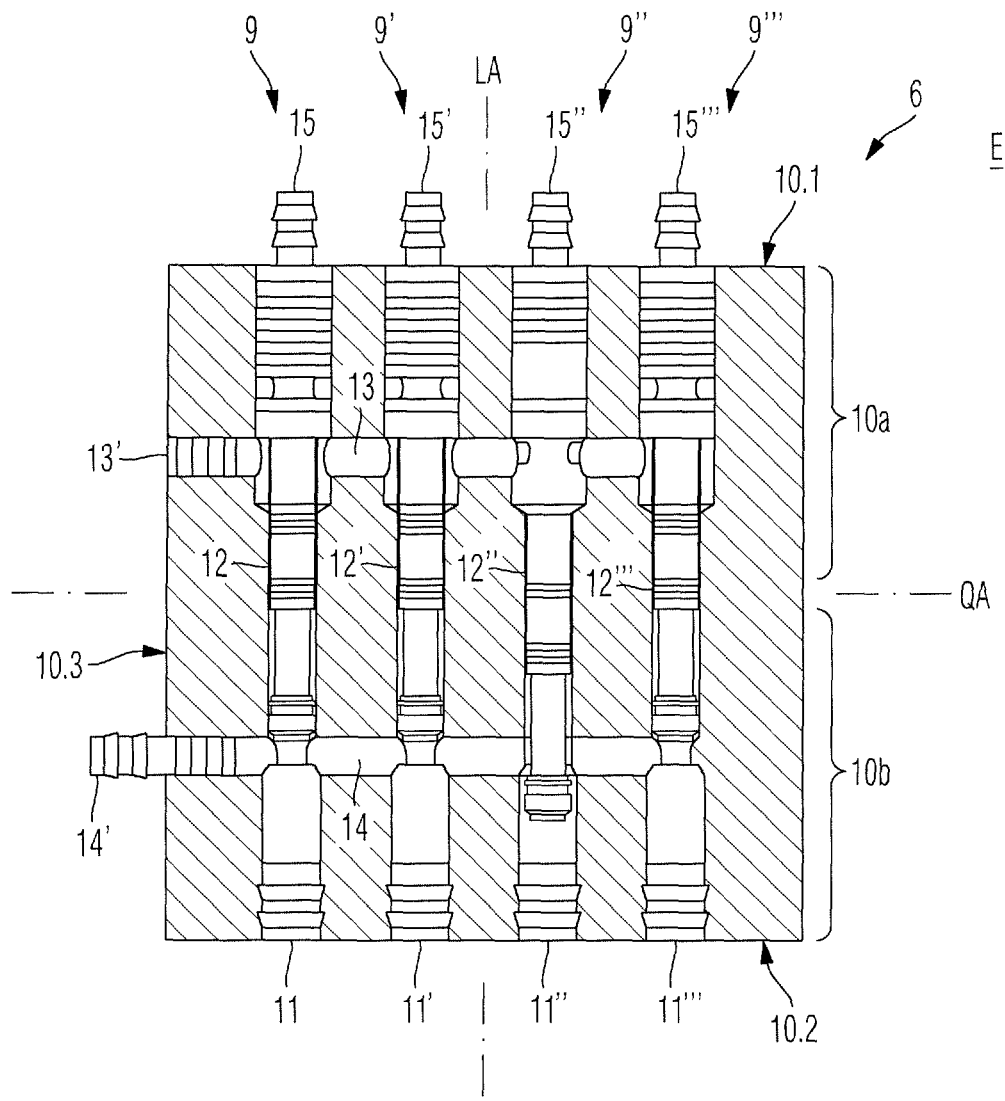
FIG. 4 shows a longitudinal section through the valve mechanism of FIG. 3 according to the invention.

FIG. 3 shows a perspective representation of a valve mechanism 6, according to the invention, comprising a plurality of sliding valve units 9, 9', 9", 9'" that can be switched by being pressurized with switching compressed air. The sliding valve units 9, 9', 9", 9'", in the present alternate embodiment, are accommodated in a valve body 10, which is manufactured in the form of a one-piece hexahedral preformed body of plastic or metal. In an alternative embodiment, according to FIGS. 9 to 13, instead of the one unitary valve body 10, a valve body system 100 is provided, which has a modular design, i.e. the valve body system 100 comprises a plurality of valve body modules, namely a first, second and third valve body module 100.1 to 100.3.

In the present exemplary embodiment according to FIG. 3, first to fourth pneumatically switchable sliding valve units 9, 9', 9", 9'" are provided, which are accommodated in the valve body 10. The valve body 10 has a one-piece design and is manufactured from a plastic material, namely by an injection molding process. Following the injection molding process, the block-like preformed body is subjected to a machining process in which a plurality of valve bores 11, 11', 11", 11'" are produced in the base body, which extend along the longitudinal axis LA of the block-shaped preformed body and/or valve body 10 from the top side 10.1 to its bottom side 10.2.

In the present embodiment, first to fourth valve bores 11, 11', 11", 11'" are provided, in which one sliding valve piston 12, 12', 12", 12'" is axially guided, i.e. the valve mechanism 6 depicted in FIGS. 3 to 6 comprises first to fourth sliding valve pistons 12, 12', 12", 12'". One valve bore 11, 11', 11", 11'" together with the therein guided sliding valve pistons 12, 12', 12", 12'" constitutes respectively one pneumatically switchable sliding valve unit 9, 9', 9", 9'".

In the present embodiment, the valve mechanism 6 comprises one first sliding valve unit 9 with one first valve bore 11 and one first therein guided sliding valve piston 12, one second sliding valve unit 9' with one second valve bore 11' and one second therein guided sliding valve piston 12', one third sliding valve unit 9" with one third valve bore 11" and one third therein guided sliding valve piston 12" and one fourth sliding valve unit 9'" with one fourth valve bore 11'" and one fourth therein guided sliding valve piston 12'".

Figure 7:
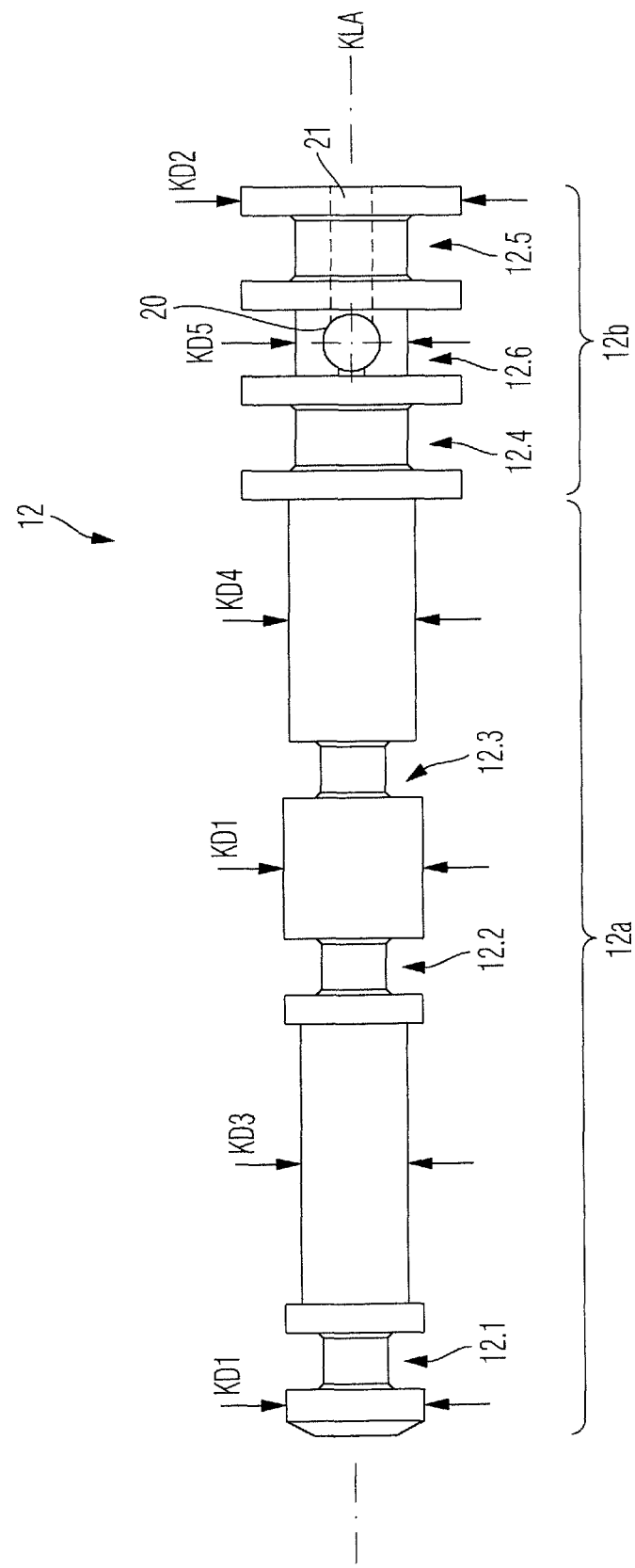
FIG. 7 shows a side view of an alternate embodiment of a sliding valve piston.

FIG. 7 depicts a side view of such a sliding valve piston 12, 12', 12", 12'". The four sliding valve units 9, 9', 9", 9'", depicted in FIGS. 3 to 6 respectively, comprise one sliding valve piston 12, 12', 12", 12'" having an identical design. The valve bores 11, 11', 11", 11'" are arranged parallel and at a distance to each other and to the longitudinal axis LA of the common valve body 10 in a plane E. They likewise have an identical course of the bore cross section along the longitudinal axis LA.

In the present embodiment, the first to fourth valve bores 11, 11', 11", 11'" respectively extend from the top side 10.1 of the hexahedral valve body 10 to the bottom side 10.2 of the hexahedral valve body 10, i.e. they completely penetrate the valve body 10 along the longitudinal axis LA. The first to fourth valve bores 11, 11', 11", 11'" are connected with each other by a first connection bore 13 extending parallel to the transverse axis QA of the valve body 10 in the upper valve body half 10a. The first connection bore 13 extends in this embodiment likewise in the plane E and preferably perpendicular to the longitudinal axis LA.

Further, in the lower valve body half 10a a second connection bore 14 is provided, which connects the first to fourth valve bores 11, 11', 11", 11'" with each other and extends in the plane E and along the transverse axis QA. By the first and second connection bore 13, 14, pneumatic switching paths are provided for controlling the sliding valve units 9, 9', 9", 9'" within the valve body 10. For this purpose the sliding valve units 9, 9', 9", 9'" are designed as multi-port valves.

The valve mechanism 6, according to the invention, comprises on the top side 10.1 of the valve body 10 a plurality of control connections 15, 15', 15", 15'", which are connected to the upper openings of the first to fourth valve bores 11, 11', 11", 11'". By the latter, each sliding valve unit 9, 9', 9", 9'" can be supplied with switching compressed air, therefore making possible a pneumatic switching of the corresponding sliding valve unit 9, 9', 9", 9'" by pressurization with switching compressed air, which causes an axial displacement of the respective sliding valve piston 12, 12', 12", 12'". The lower openings of the first to fourth valve bores 11, 11', 11", 11'" provided on the bottom side 10.2 of the valve body 10 are provided with sealing means in the present embodiment, which produces a fluid- and air-tight seal of the lower openings of the valve bores 11, 11', 11", 11'".

The first connection bore 13 constitutes a first side opening 13' on one transverse side 10.3 of the valve body 10 and extends from this first side opening 13' along the transverse axis QA up until the fourth valve bore 11'". The first connection bore 13 connects the connection bores 11, 11', 11", 11'" with each other in the upper valve body half 10a. The first side opening 13' in the present embodiment is provided with a sealing means, so that a closed first connecting canal is established between the connection bores 11, 11', 11", 11'" in the upper area of the valve body 10.

The second connection bore extends analogously to the first connection bore 13 from a second side opening 14' provided in the transverse side 10.3 of the valve body 10 in the direction of the transverse axis QA up to the fourth valve bore 11'". The second connection bore 14 connects the connection bores 11, 11', 11", 11'" with each other in the lower valve body half 10b. In the second side opening 14', a compressed air connection 16 is provided, by which continuous compressed air is supplied via the connection bore 14 to the valve bores 11, 11', 11", 11'". Depending on the current switching state of the sliding valve units 9, 9', 9", 9'", the supplied continuous compressed air is conducted to side switching outputs 17, 17', 17", 17'", which are provided on the longitudinal side 10.4 of the valve body 10. The switching outputs 17, 17', 17", 17'" are connected by connection bores 18, 18', 18", 18'" with the respective valve bores 11, 11', 11", 11'", whereby the connection bores 18, 18', 18", 18'" extend respectively from valve bores 11, 11', 11", 11'" to the longitudinal side 10.4 of the valve body 10. For example, the first valve bore 11 is connected by a first connection bore 18 with a first switching output 17, the second valve bore 11' by means of a second connection bore 18' with a second switching output 17', the third valve bore 11" by means of a third connection bore 18" with a third switching output 17" and the fourth valve bore 11'" by means of a fourth connection bore 18'" with a fourth switching output 17'". Finally, above the first to fourth connections bores 18, 18', 18", 18'" respectively one ventilation bore 19, 19', 19", 19'" is provided, which extends from the respective valve bore 11, 11', 11", 11'" perpendicular to the plane E to the front side 10.4 of the valve body 10. These are preferably provided in the transition area between the upper and lower valve body half 10*a*, 10*b*.

The sliding valve units 9, 9', 9", 9'", in the present embodiment, have a first switching state and a second switching state, respectively, which results from an axial displacement of the corresponding sliding valve piston 12, 12', 12", 12'". In the first switching state the sliding valve piston 12, 12', 12", 12'" is in the upper area of the valve body 10 and therefore closes the respective switching output 17, 17', 17", 17'", i.e. the continuous compressed air supplied via the second connection bore 14 is not conducted to the respective switching output 17, 17', 17", 17'", since the corresponding valve path of the lower free end section of the sliding valve piston 12, 12', 12", 12'" is closed. In the second switching state the sliding valve piston 12, 12', 12", 12'" is in the lower area of the valve body 10 and in this position releases the valve path between the second connection bore 14, the corresponding section of the valve bores 11, 11', 11", 11'" via the connection bores 18, 18', 18", 18'" to the respective switching output 17, 17', 17", 17'", i.e. the sliding valve unit 9, 9', 9", 9'" is opened and the supplied continuous compressed air is conducted to the released switching output 17, 17', 17", 17'". Simultaneously, in the second switching state, the switching compressed air supplied via the respective control input 15, 15', 15", 15'" is conducted via the first connection bore 13 into the adjacent valve bores 11, 11', 11", 11'", therefore locking the latter.

For provision of the different valve paths, the sliding valve pistons 12, 12', 12", 12'" have a corresponding profiling, which depending on the switching state of the sliding valve unit 9, 9', 9", 9'" and/or on the axial position of the sliding valve piston 12, 12', 12", 12'" in the corresponding valve bore 11, 11', 11", 11'", releases a valve path between the second connection bore 14 and the switching output 17, 17', 17", 17'" corresponding to the sliding valve unit 9, 9', 9", 9'", so that the released switching output 17, 17', 17", 17'" is pressurized with continuous compressed air. From the switching output 17, 17', 17", 17'" the continuous compressed air is supplied via the connected supply hose 4, 4', 4", 4'" to the corresponding dental instrument 5, 5', 5", 5'". The ventilation bore 19, 19', 19", 19'" provided respectively above the switching output 17, 17', 17", 17'" enables closing of the actuated sliding valve unit 9, 9', 9", 9'" after switching off the switching compressed air, namely allowing the respectively supplied continuous compressed air to escape and therefore closing of the sliding valve unit 9, 9', 9", 9'" due to axial displacement of the corresponding sliding valve piston 12, 12', 12", 12'" along the longitudinal axis LA upward, i.e. in the direction of the control connections 15, 15', 15", 15'".

The switching compressed air is supplied in a preferred embodiment to the control input 15, 15', 15", 15'" whose corresponding dental instrument 5, 5', 5", 5'" is removed from the holder element 7, 7', 7", 7'". For this purpose, the switching compressed air is either released by the switching element 8, 8', 8", 8'" directly to the corresponding control input 15, 15', 15", 15'" or a switching pulse is generated with which such a release is controlled, i.e. the supplied switching compressed air is released to the control input 15, 15', 15", 15'". By appropriate switching of the corresponding sliding valve unit 9, 9', 9", 9'", the continuous compressed air supplied to the valve mechanism 6 is conducted to the corresponding dental instrument 5, 5', 5", 5'". The remaining additional dental instruments 5, 5', 5", 5'" are not supplied with continuous compressed air, resulting in a safety shut-off.

In FIGS. 3 to 6, the third sliding valve unit 9" is pressurized with switching compressed air and thereby switched from the first to the second switching state. The remaining first, second and fourth sliding valve unit 9, 9', 9'" continue to be in the first switching state. The continuous compressed air supplied via the second connection bore 14 to the third valve bore 11" can be conducted to the third switching output 17" via the valve path released by the third sliding valve piston 12", to which (switching output) the third dental instrument 5" is connected directly or indirectly by the third supply hose 4". By the switching compressed air supplied via the first connection bore 13, the first, second and fourth sliding valve pistons 12, 12', 12", due to their profiling, are pressed upward, i.e. in the direction of the respective control input 15, 15', 15'" and therefore the first, second and fourth sliding valve unit 9, 9', 9'" are locked in the first switching state.

FIG. 7 shows an alternate embodiment of a sliding valve piston 12. The first sliding valve piston 12 comprises a first piston section 12*a* and a second piston section 12*b* having different piston diameters, whereby the first piston section 12*a* extends approximately over two-thirds of the total length of the sliding valve piston 12 and the second piston section 12*b* thereon adjoining extends over the remaining third of the total length of the sliding valve piston 12. The first piston section 12*a* has a first piston diameter KD1 and the second piston section 12*b* has a second piston diameter KD2, whereby in the first piston diameter is smaller than the second piston diameter KD2. For example, the first piston diameter KD1 is between 2 mm and 3 mm, preferably 2.3 mm and the second piston diameter KD2 is between 3.5 mm and 4.5 mm, preferably 3.9 mm.

Further, the first piston section 12*a* is provided with a first to third circumferential groove 12.1 to 12.3 and the second piston section 12*b* is provided with a fourth and fifth circumferential groove 12.4, 12.5, which are for accommodating sealing rings, especially sealing O-rings. The diameter of the sliding valve piston 12 in the area of the first to third groove 12.1 to 12.3 is, for example, approximately 1.1 mm and in the area of the fourth and fifth groove 12.4, 12.5 is approximately 2 mm.

Between the first and second circumferential groove 12.1, 12.2 the first piston section 12*a* has a reduced third piston diameter KD3 compared to the first piston diameter KD1, the third piston diameter being approximately 1.8 mm. The diameter of the first piston section between the second and third circumferential groove 12.2, 12.3 corresponds to the first piston diameter KD1. The part of the first piston section 12*a* adjoining the third circumferential groove 12.3 in the direction of the second piston section 12*b* has a reduced fourth piston diameter KD4 compared to the first piston diameter KD1, the fourth piston diameter being approximately 2.2 mm.

Between the fourth and fifth groove 12.4, 12.5 the second piston section 12*b* comprises a sixth circumferential groove 12.6 having a fifth piston diameter KD5. The second piston section 12*b* has a first piston through-bore 20 extending perpendicular to the piston longitudinal axis KLA and a second piston through-bore 21 extending along the piston longitudinal axis KLA, whereby the second piston through-bore 21 extends from the end face of the second piston section 12*b* into the first piston through-bore 20. The sixth circumferential groove 12.6 constitutes together with the inner surface of the valve bore 11, 11', 11", 11'" a ring-shaped valve chamber.

Figure 5:
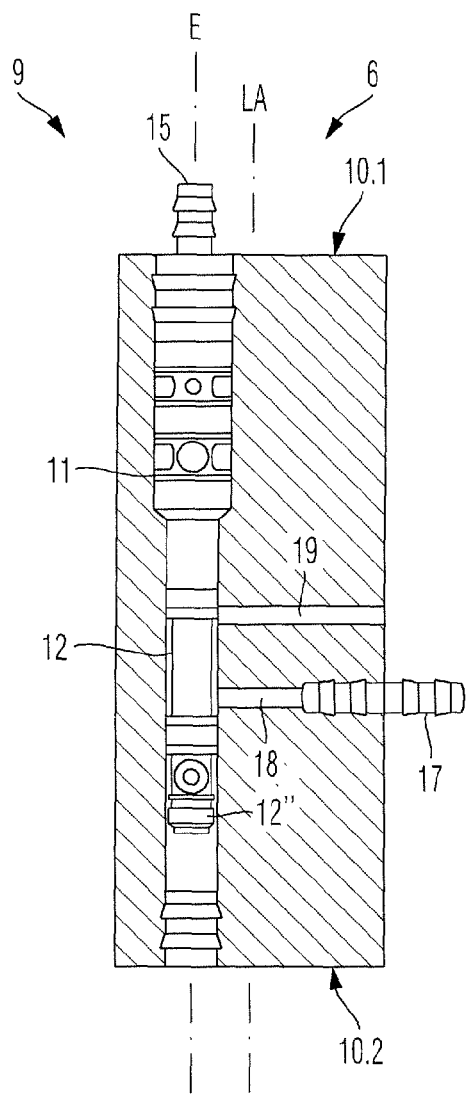
FIG. 5 shows a cross section through the valve mechanism of FIG. 3 according to the invention.
Figure 6:
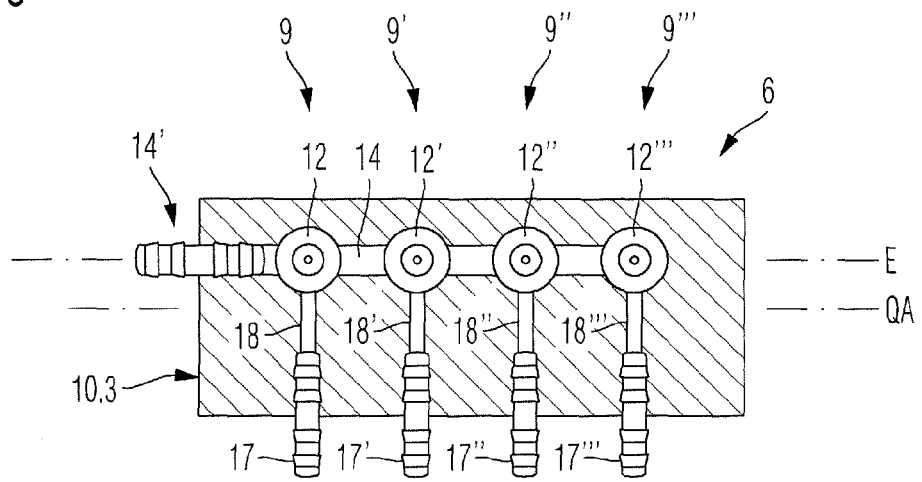
FIG. 6 shows a section through the valve mechanism of FIG. 3 according to the invention along a plane extending perpendicular to the longitudinal axis.
Figure 8:
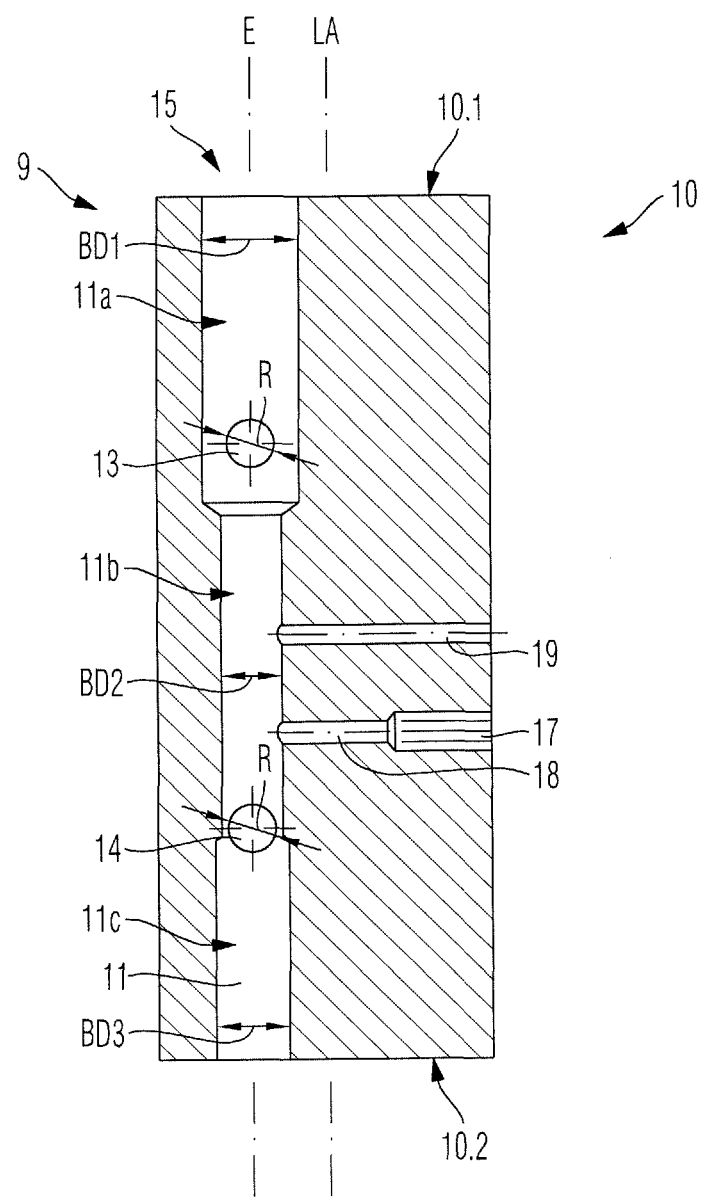
FIG. 8 shows a cross section through the valve mechanism of FIG. 3 according to the invention without a sliding valve piston.

FIG. 8 depicts analogously to FIG. 5 a section along longitudinal axis LA through a valve body 10 according to the invention without therein accommodated sliding valve pistons 12, 12', 12", 12'". This depiction exemplifies the course of the cross section of the valve bore 11, 11', 11", 11'" along the longitudinal axis LA, which is adapted to the embodiment of the sliding valve piston 12 depicted in FIG. 7. The valve bore 11 comprises a first, second and third valve bore section 11a through 11c, which adjoin each other along the longitudinal axis LA and have a different bore diameter, respectively, namely the first valve bore section 11a has a first bore diameter BD1, the second valve bore section 11b has a second bore diameter BD2 and the third valve bore section 11c has a third bore diameter BD3.

In the present embodiment, the second bore diameter BD2 is smaller than the first and third bore diameter BD1, BD3 and the third bore diameter BD3 is smaller than the first bore diameter BD1, namely the first bore diameter BD1 is for example approximately 4 mm, the second bore diameter BD2 is approximately 2.5 mm and the third bore diameter BD3 is approximately 3 mm. The connection bores 18, 18', 18", 18'" and the ventilation bores 19, 19', 19", 19'" are connected in the area of the second valve bore section 11b with the valve bore 11, 11', 11", 11'". Further, the first and second connection bore 13, 14 in the present exemplary embodiment have a radius R of approximately 2 mm.

In the first closed switching state of the sliding valve unit 9, 9', 9", 9'", the first piston section 12a is accommodated in the second valve bore section 11b, i.e. the second valve bore section 11b is closed toward the bottom due to the sealing ring provided in the first groove 12.1. Analogous to this, the fourth groove 12.4, with therein accommodated sealing ring, is above the first connection bore 13 in the first valve bore section 11a, i.e. the valve path from the control input 15, 15', 15", 15'" via the first and second piston bore 20, 21 to the first connection bore 13 is interrupted.

In the second opened switching state of the sliding valve unit 9, 9', 9", 9'", the valve path from the control input 15, 15', 15", 15'" via the first and second piston bore 20, 21 to the first connection bore 13 is opened, i.e. the switching compressed air provided for example via the third control input 15" is conducted in the first valve bore section 11a to the first, second and fourth valve bore 11, 11', 11' and pressurizes the second piston section 12b with the switching compressed air, which is thereby locked in the existing first, closed switching state.

Figure 9:
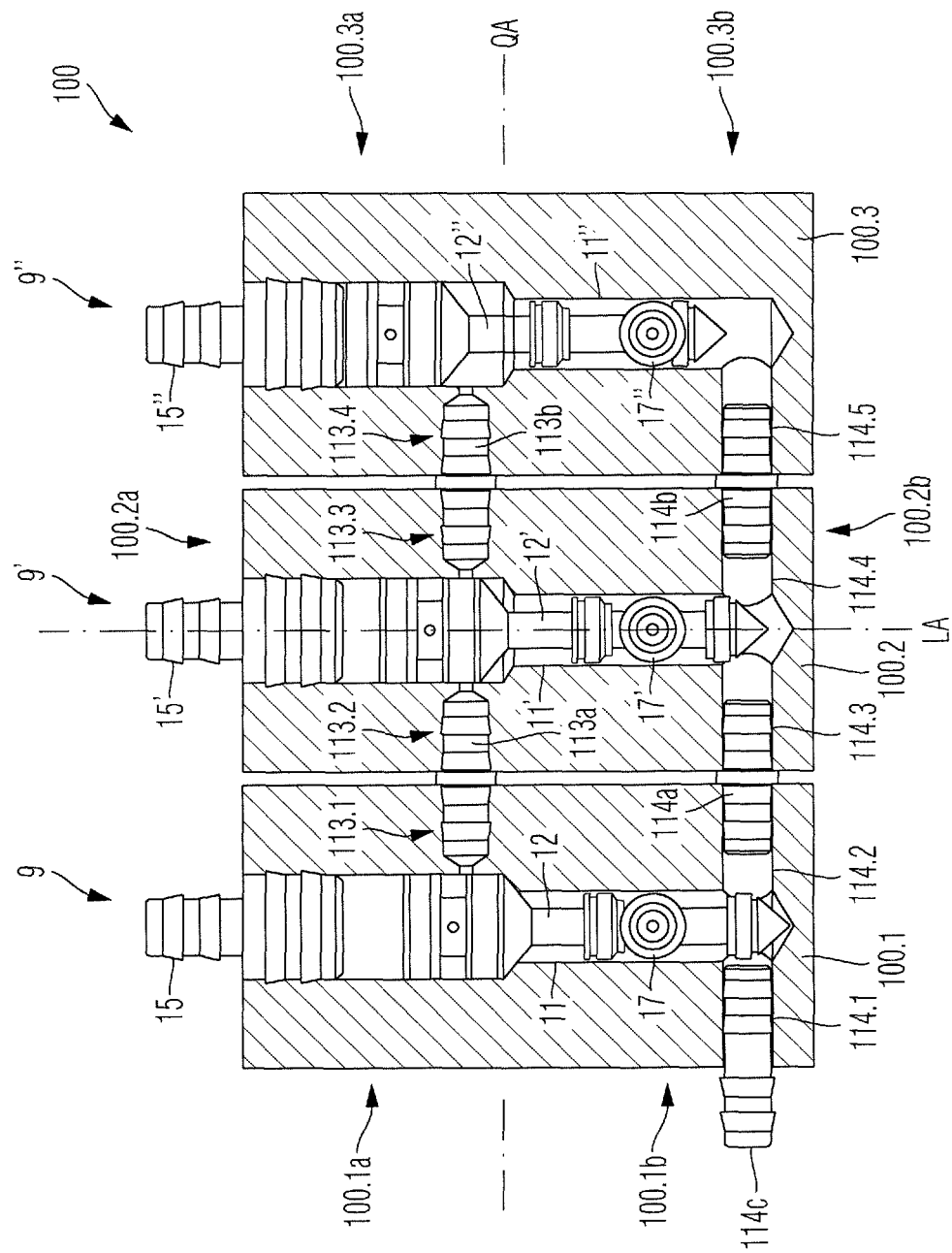
FIG. 9 shows a schematic section through an alternative embodiment of the valve mechanism according to the invention with a valve body system comprising three valve body modules.
Figure 10:
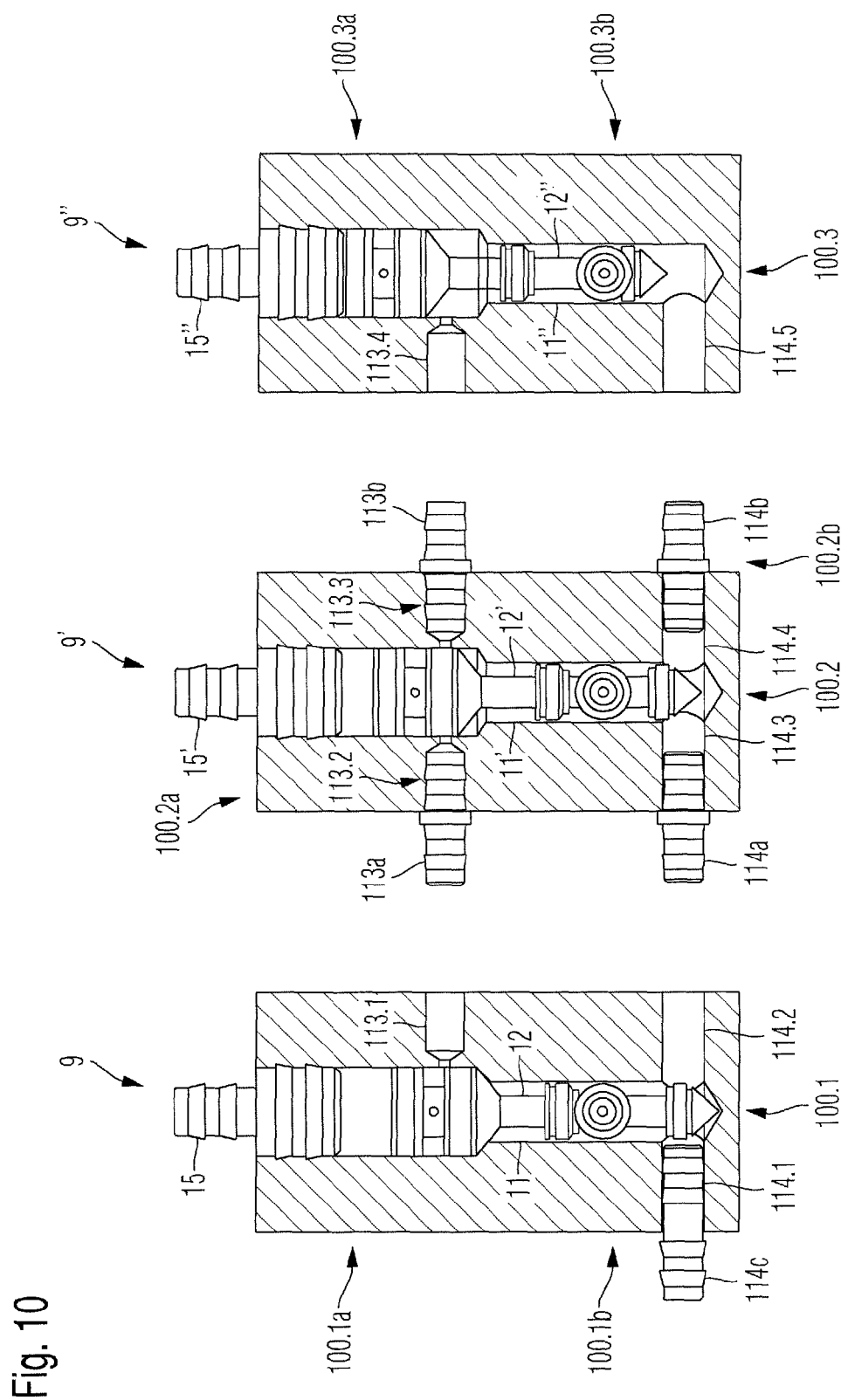
FIG. 10 shows a schematic section through an alternative embodiment of the valve mechanism of FIG. 9 according to the invention with mutually separated valve body modules.

FIGS. 9 and 10 show a schematic sectional view through an alternative embodiment of the valve mechanism 6, according to the invention, comprising a valve body system 100 having a plurality of valve body modules 100.1 to 100.3. As opposed to the embodiment described above, instead of a monolithic, i.e. one-piece design of the valve body 10, a modular design is provided, resulting in a flexible adaptation of the number of pneumatically switchable sliding valve units 9, 9', 9", 9'" in the valve mechanism 6. As a result of this design, the valve mechanism 6 can also be quickly and easily expanded to include any required additional sliding valve units 9, 9', 9", 9'". In FIGS. 9 through 13, referring to the alternative embodiment of the valve mechanism 6, equivalent elements are provided with identical reference signs.

In the present embodiment, a pneumatically switchable sliding valve unit 9, 9', 9" is accommodated in a valve body module 100.1 to 100.3, respectively, namely a first pneumatically switchable sliding valve unit 9 in the first valve body module 100.1, a second pneumatically switchable sliding valve unit 9' in the second valve body module 100.2 and a third pneumatically switchable sliding valve unit 9" in the third valve body module 100.3. The valve body modules 100.1 to 100.3 are for establishing a plug-type connection between the single modules 100.1 to 100.3 for producing a valve mechanism 6 according to the invention that provides the switching functions analogous to the foregoing exemplary embodiment.

Figure 11:
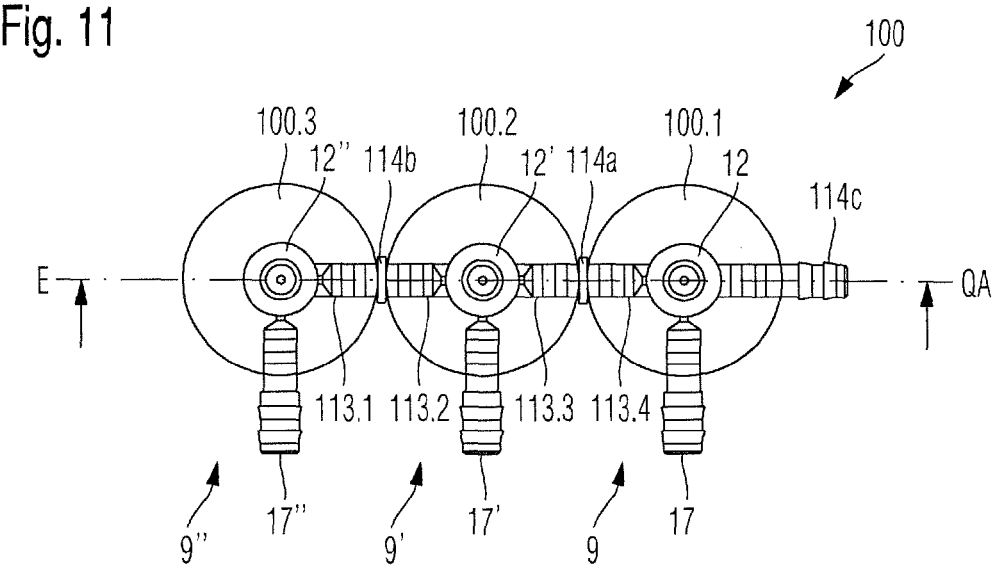
FIG. 11 shows a schematic cross section through the alternative embodiment of the valve mechanism of FIG. 9 according to the invention.
Figure 12:
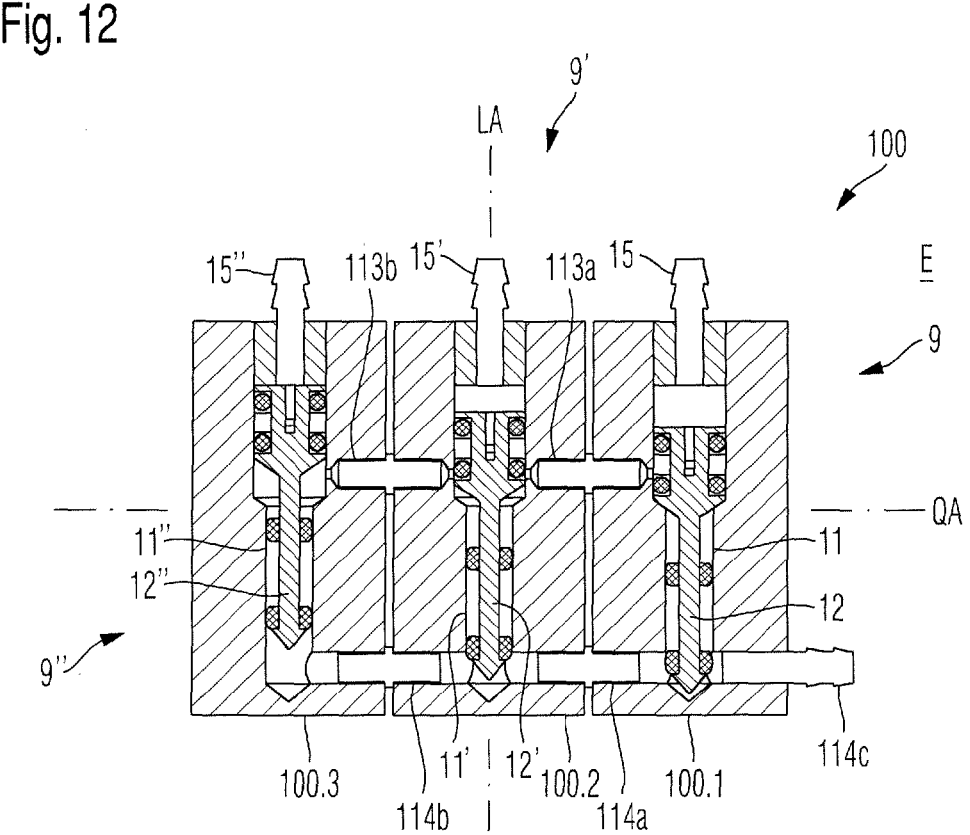
FIG. 12 shows a longitudinal section along the plane E through the valve mechanism of FIG. 11 according to the invention.

As can be seen in FIG. 11, the valve body modules 100.1 to 100.3 can be cylindrical. It goes without saying that other three-dimensional forms are possible, such as hexahedral or cuboid, which are suitable for establishing a plug-type connection between the single modules 100.1 to 100.3. The valve body modules 100.1 to 100.3 are likewise manufactured for example from plastic or metal.

A valve body module 100.1 to 100.3, according to FIGS. 9 through 12, comprises respectively a valve bore 11, 11', 11", in which a sliding valve piston 12, 12', 12", is guided axially. A valve bore 11, 11', 11" together with the therein guided sliding valve piston 12, 12', 12" constitutes here again a pneumatically switchable sliding valve unit 9, 9', 9" respectively, which is additionally accommodated in a separate valve body module 100.1 to 100.3.

In the present embodiment therefore, the valve body module 100.1 comprises the first sliding valve unit 9 having the first valve bore 11 and the first therein guided sliding valve piston 12, the second valve body module 100.2 the second sliding valve unit 9' having the second valve bore 11' and the second therein guided sliding valve piston 12' and the third valve body module 100.3 the third sliding valve unit 9" having a third valve bore 11" and a third therein guided sliding valve piston 12".

Figure 13:
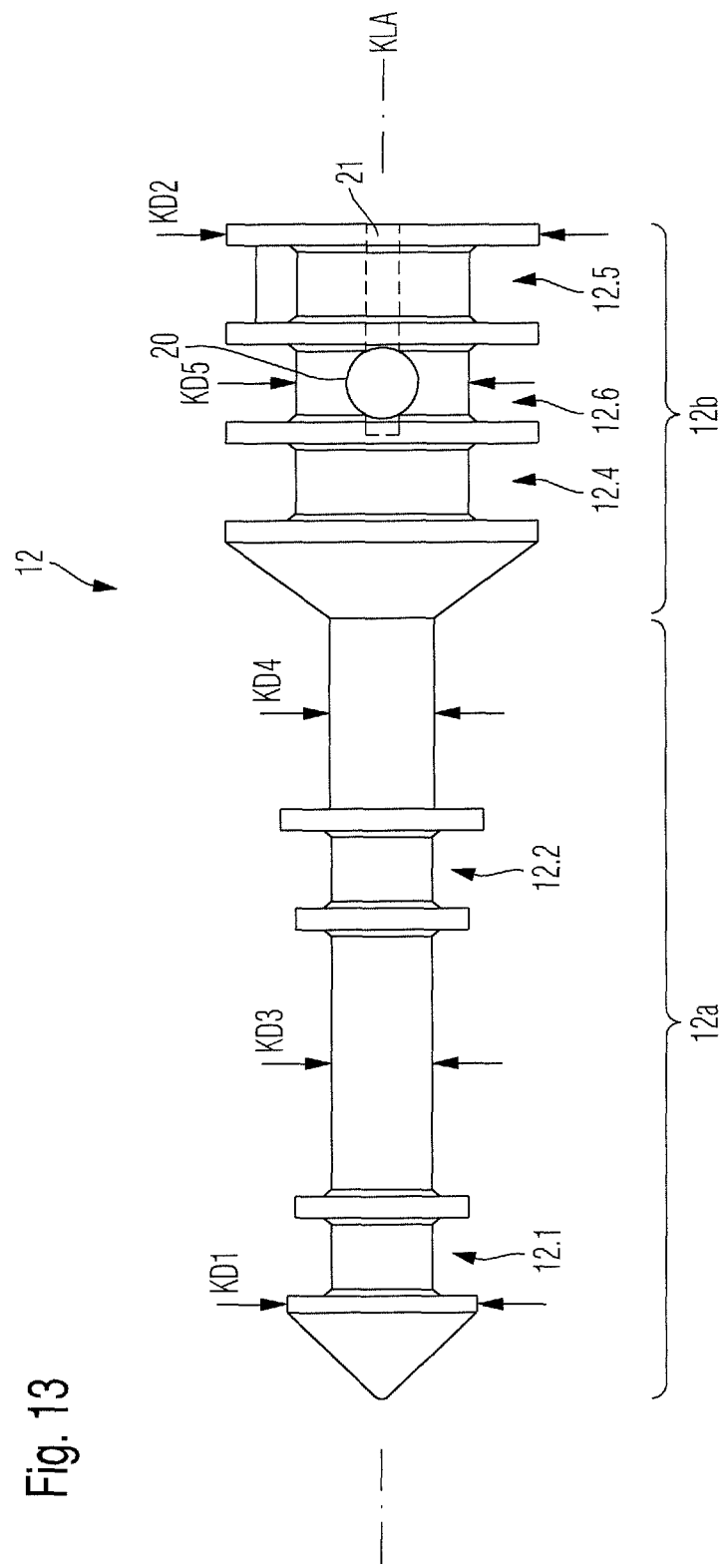
FIG. 13 shows a side view of an alternative embodiment of a sliding valve piston.

FIG. 13 shows exemplarily a side view of an alternative embodiment of a sliding valve piston 12, 12', 12", whereby the sliding valve units 9, 9', 9" depicted in FIGS. 9 to 12 respectively, comprise a sliding valve piston 12, 12', 12" of identical design. In mounted state, the valve bores 11, 11', 11" of the valve body modules 100.1 b is 100.3 extend parallel to each other and to the longitudinal axis LA of the valve body system 100. The valve bores 11, 11', 11" have an identical course of the bore cross section.

The first to third valve bores 11, 11', 11" extend from the top side of a valve body module 100.1 to 100.3 via the upper valve module half 100.1a, 100.2a, 100.3a into the lower valve body module half 100.1b, 100.2b, 100.3b, however, as opposed to the foregoing exemplary embodiment, they do not completely penetrate the respective valve body module 100.1 to 100.3, but are implemented in the manner of a blind hole bore.

The first to third valve bores 11, 11', 11" can be connected with each other by means of first connection bore sections 113.1, 113.2, 113.3, 113.4 extending parallel to the transverse axis QA of the respective valve body module 100.1 to 100.3 in the respective upper valve body module half 100.1a, 100.2a, 100.3a, namely by tubular first connection elements 113a, 113b. In mounted state, the first connection bore sections 113.1, 113.2, 113.3, 113.4 therefore constitute a continuous, closed connection bore analogous to the first connection bore 13, which extends in the plane E, and the first to third valve bore 11, 11', 11".

In the lower valve body module half 100.1b, 100.2b, 100.3b, second connection bore sections 114.1, 114.2, 114.3, 114.4 and 114.5 are provided which make it possible to establish a connection between the first to third valve bore 11, 11', 11" and extend in the plane E and along the transverse axis QA. For connecting the second connection bore sections 114.1, 114.2, 114.3, 114.4 and 114.5, tubular second plug-type connecting elements 114a, 114b and a tubular connecting element 114c are provided. The second connection bore sections 114.1, 114.2, 114.3, 114.4 and 114.5 produce a connection between the valve bores 11, 11', 11" comparable to the second connection bore 14 of the first exemplary embodiment.

By the first and second connection bore sections 113.1, 113.2, 113.3, 113.4, 114.1, 114.2, 114.3, 114.4 and 114.5 pneumatic switching paths are provided for controlling the sliding valve units 9, 9', 9" within the valve body system 100. Analogously, the sliding valve units 9, 9', 9" are designed as multi-port valves.

The valve mechanism 6, according to the invention, comprises on the respective top side of a valve body module 100.1 to 100.3 a control connection 15, 15', 15", which is connected to the upper opening of the first to third valve bore 11, 11', 11". By the latter, each sliding valve unit 9, 9', 9" can be supplied with switching compressed air, therefore making possible a pneumatic switching of the corresponding sliding valve unit 9, 9', 9" by pressurization with switching compressed air, which causes an axial displacement of the respective sliding valve piston 12, 12', 12".

Depending on the current switching state of the sliding valve units 9, 9', 9", the supplied continuous compressed air is conducted to side switching outputs 17, 17', 17", which are provided on the longitudinal sides of the valve body modules 100.1 to 100.3. The switching outputs 17, 17', 17" are connected by connection bores 18, 18', 18" with the respective valve bores 11, 11', 11", whereby the connection bores 18, 18', 18" (not visible in FIGS. 9 to 12) extend respectively from valve bores 11, 11', 11" to the longitudinal side of a valve body module 100.1 to 100.3.

The sliding valve units 9, 9', 9" in the second embodiment also have a first and second switching state, which results from an axial displacement of the corresponding sliding valve piston 12, 12', 12". In the first switching state the sliding valve piston 12, 12', 12" is in the upper area of the valve body module 100.1 to 100.3 and therefore closes the respective switching output 17, 17', 17", i.e. the continuous compressed air supplied via the second connection bore sections 114.1, 114.2, 114.3, 114.4 and 114.5 is not conducted to the respective switching output 17, 17', 17", since the corresponding valve path of the lower free end section of the sliding valve piston 12, 12', 12" is closed.

In the second switching state, the sliding valve piston 12, 12', 12" is in the lower area of the valve body module 100.1 to 100.3 and in this position releases the valve path between the second connection bore sections 114.1, 114.2, 114.3, 114.4 and 114.5, the corresponding section of the valve bores 11, 11', 11" via the connection bores 18, 18', 18" to the respective switching output 17, 17', 17", i.e. the sliding valve unit 9, 9', 9" is opened and the supplied continuous compressed air is conducted to the released switching output 17, 17', 17". Simultaneously in the second switching state, the switching compressed air supplied via the respective control input 15, 15', 15" is conducted via the first connection bore sections 113.1, 113.2, 113.3, 113.4 into the adjacent valve bores 11, 11', 11", therefore locking the latter.

FIG. 13 shows an alternative embodiment of a sliding valve piston 12. The first sliding valve piston 12 comprises a first piston section 12a and a second piston section 12b having different piston diameters, whereby the first piston section 12a extends approximately over two-thirds of the total length of the sliding valve piston 12 and the second piston section 12b thereon adjoining extends over the remaining third of the total length of the sliding valve piston 12.

The first piston section 12a has a first piston diameter KD1 and the second piston section 12b has a second piston diameter KD2, whereby in a preferred embodiment, the first piston diameter is smaller than the second piston diameter KD2. For example, the first piston diameter KD1 is between 2 mm and 3 mm, preferably 2.3 mm and the second piston diameter KD2 is between 3.5 mm and 4.5 mm, preferably 3.9 mm.

As opposed to the embodiment of FIG. 7, the first piston section 12a is provided only with the first and second circumferential groove 12.1, 12.2 and the second piston section 12b is provided with the fourth and fifth circumferential groove 12.4, 12.5, which are for accommodating sealing rings, especially O-rings.

Between the first and second circumferential groove 12.1, 12.2, the first piston section 12a has a reduced third piston diameter KD3 compared to the first piston diameter KD1, the third piston diameter being for example approximately 108 mm. The part of the first piston section 12a adjoining the second circumferential groove 12.2 in the direction of the second piston section 12b has a reduced fourth piston diameter KD4 compared to the first piston diameter KD1, the fourth piston diameter corresponding to the third piston diameter KD3.

Between the fourth and fifth groove 12.4, 12.5, the second piston section 12b comprises a sixth circumferential groove 12.6 having a fifth piston diameter KD5. The second piston section 12b has a first piston through-bore 20 extending perpendicular to the piston longitudinal axis KLA and a second piston through-bore 21 extending along the piston longitudinal axis KLA, whereby the second piston through-bore 21 extends from the end face of the second piston section 12b into the first piston through-bore 20. The sixth circumferential groove 12.6 constitutes together with the inner surface of the valve bore 11, 11', 11" a ring-shaped valve chamber. As opposed to the embodiment of FIG. 7, the transition area between the first and second piston section 12a, 12b has a conical course.

Figure 14:
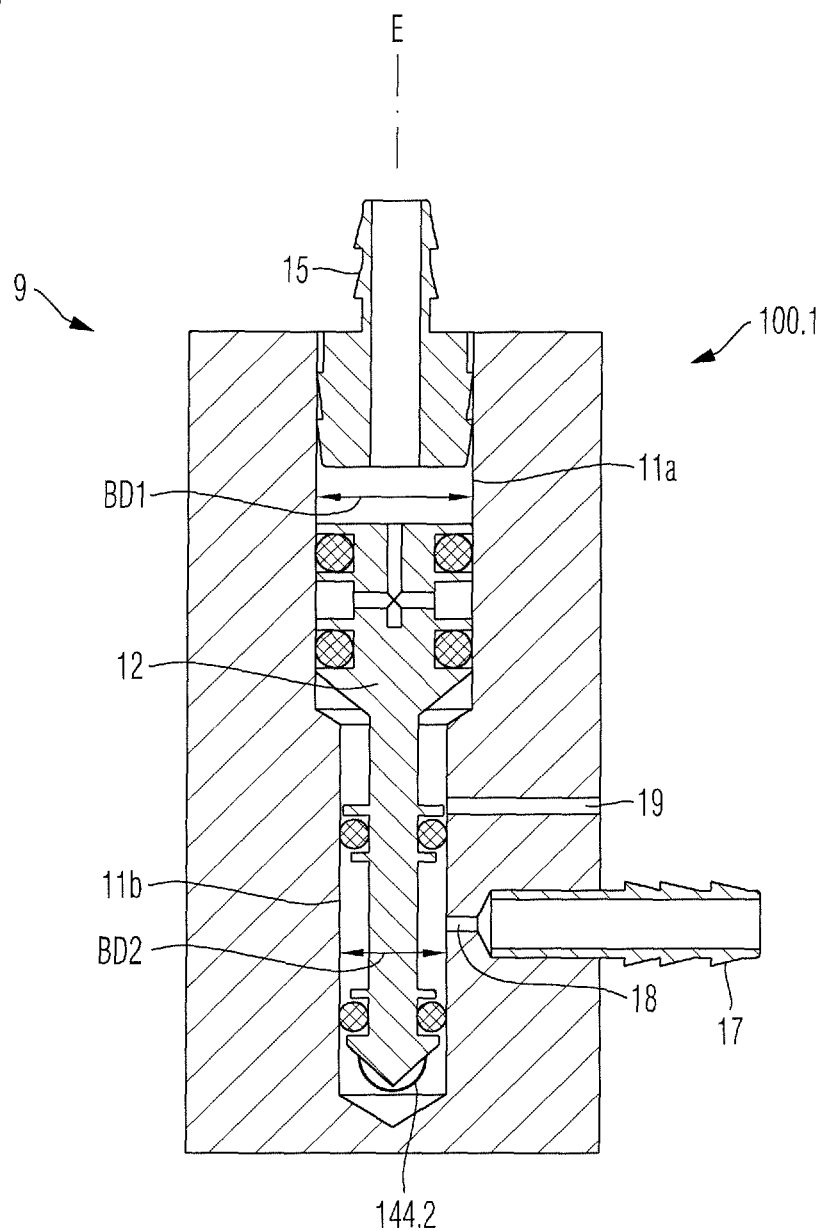
FIG. 14 shows a cross section through a valve body module.

FIG. 14 depicts, analogously to FIG. 8, a section along longitudinal axis LA through a valve body module 100.1 according to the invention. As opposed to the first exemplary embodiment, the valve bore 11 comprises only a first and second valve bore section 11a, 11b, which adjoin each other along the longitudinal axis LA and have a different bore diameter, respectively. The first valve bore section 11a has a first bore diameter BD1 and the second valve bore section 11b has a second bore diameter BD2, whereby the second bore diameter BD2 is smaller than the first bore diameter BD1.

The invention was described above based on an exemplary embodiment. It goes without saying that numerous variations and modifications of the invention are possible without abandoning the underlying inventive concept.

REFERENCE LIST 1 dental device
2 supply and control unit
3 wheeled cart
4, 4', 4", 4'" first to fourth supply hose
5, 5', 5", 5'" first to fourth dental instrument
6 valve mechanism
7, 7', 7", 7'" first to fourth holding element
8, 8', 8", 8'" first to fourth switching element
9, 9', 9", 9'" first to fourth sliding valve unit
10 valve body
10a upper valve body half
10b lower valve body half
10.1 top side
10.2 bottom side 10.3 transverse side
10.4 longitudinal side
11, 11', 11", 11'" first to fourth valve bore
11a first valve bore section
11b second valve bore section
11c third valve bore section
12, 12', 12", 12'" first to fourth sliding valve piston
12a first piston section
12b second piston section
12.1 first circumferential groove
12.2 second circumferential groove
12.3 third circumferential groove
12.4 fourth circumferential groove
12.5 fifth circumferential groove
12.6 sixth circumferential groove
13 first connection bore
13' first side opening
14 second connection bore
14' second side opening
15, 15', 15", 15'" first to fourth control input
16 compressed air connection
17, 17', 17", 17'" first to fourth switch output
18, 18', 18", 18'" first to fourth connection bore
19, 19', 19", 19'" first to fourth ventilation bore
20 first piston bore
21 second piston bore
100 valve body system
100.1 first valve body module
100.2 second valve body module
100.3 third valve body module
100.1a, 100.2a, 100.3a upper valve body module halves
100.1b, 100.2b, 100.3b lower valve body module halves
113.1, 113.2, 113.3, 113.4 first connection bore sections
113a, 113b first tubular plug-in connecting elements
114.1, 114.2, 114.3, 114.4, 114.5 second connection bore sections
114a, 114b second tubular plug-in connecting elements
114c tubular connecting element
BD1 first bore diameter
BD2 second bore diameter
BD3 third bore diameter
KD1 first piston diameter
KD2 second piston diameter
KD3 third piston diameter
KD4 fourth piston diameter
KD5 fifth piston diameter
KLA piston longitudinal axis
LA longitudinal axis
E plane
QA transverse axis
R radius

What is claimed is:

1. A device for the controlled supply of compressed air to at least one pneumatically operated dental instrument from a supply and control unit wherein the at least one pneumatically operated dental instrument is connected by a compressed air supply hose with a valve mechanism in the supply and control unit, the valve mechanism comprising:
a plurality of pneumatic sliding valve units, the plurality of pneumatic sliding valve units of the valve mechanism is accommodated in one valve body, the one valve body having a single monolithic one-piece construction, the one valve body comprises a plurality of control inputs and valve bores, and each of the plurality of pneumatic sliding valve units corresponds to one of the plurality of control inputs, the plurality of control inputs are connected to openings of valve bores of the one valve body,
whereby pressurization of one of the plurality of control inputs with switching compressed air opens a corresponding one of the plurality of pneumatic sliding valve units and locks all additional pneumatic sliding valve units in a closed state, wherein for providing pneumatic switching paths within the one valve body for controlling the sliding valve units, the valve bores are connected with each other via a first connection bore in an upper valve body half and a second connection bore in a second valve body half, wherein the second connection bore is provided for a supply of continuous compressed air to the valve bores, and wherein each of the sliding valve units comprises a first piston section and a second piston section having a plurality of section-wise different piston diameters and a plurality of circumferential grooves, and the second piston section is provided with first and second bores, the first and second bores extend perpendicular to one another and constitute a part of a valve path, the valve path is open from the control input via the first and second bores to the first connection bore when a sliding valve is open.

2. The device according to claim 1, wherein the valve bore extends from a top side of the one valve body to a bottom side of the one valve body.

3. The device according to claim 1, wherein the at least one valve body is modular and comprises a plurality of valve body modules, whereby the plurality of valve body modules are connected with each other by a plug-type connection to produce a valve body system.

4. The device according to one of the claim 1, wherein each of the plurality of pneumatic sliding valve units has at least one switch output next to respective ones of the plurality of control inputs.

5. The device according to claim 1, wherein each of the plurality of pneumatic sliding valve units is switched on singly by pressurization of one of the plurality of control inputs with compressed air, by axial displacement of the profiled sliding valve piston in the valve bore along a longitudinal axis (LA) of the one valve body.

6. The device according to claim 1, wherein the valve bore comprises first and second valve bore sections having different bore diameters.

7. The device according to claim 1, wherein a profiling of the profiled sliding valve piston continues along a course of a bore cross section of the valve bore.

8. The device according to claim 1, wherein the plurality of circumferential grooves comprises first and second circumferential grooves on the first piston section, a third circumferential groove between the first piston section and the second piston section, and fourth and fifth circumferential grooves on the second piston section, whereby the plurality of circumferential grooves are for accommodating a sealing ring.

9. The device according to claim 1, further comprising a plurality of holder elements for fastening the at least one pneumatically operated dental instrument on the supply and control unit, whereby one dental instrument corresponds to one holder element.

10. The device according to claim 9, wherein the one holder element has a corresponding switch element, which is actuated by inserting the one dental instrument into the one holder element or removing the one dental instrument from the one holder element.

11. The device according to claim 10, wherein the one switch element controls a pressurization of the control inputs with switching compressed air.

12. A valve mechanism for use in a device for the controlled supply of compressed air to at least one pneumatically operated dental instrument from a supply and control unit comprising;
- a plurality of pneumatic sliding valve units, the plurality of pneumatic sliding valve units of the valve mechanism is accommodated in one valve body, the one valve body having a single monolithic one-piece construction, the one valve body comprises a plurality of control inputs and valve bores, and each of the plurality of pneumatic sliding valve units corresponds to one of the plurality of control inputs, the plurality of control inputs are connected to openings of valve bores of the one valve body,
- whereby pressurization of one of the plurality of control inputs with switching compressed air opens a corresponding one of the plurality of pneumatic sliding valve units and locks all additional pneumatic sliding valve units in a closed state, wherein for providing pneumatic switching paths within the one valve body for controlling the sliding valve units, the valve bores are connected with each other via a first connection bore in an upper valve body half and a second connection bore in a second valve body half, wherein the second connection bore is provided for a supply of continuous compressed air to the valve bores, and wherein each of the sliding valve units comprises a first piston section and a second piston section having a plurality of section-wise different piston diameters and a plurality of circumferential grooves, and the second piston section is provided with first and second bores, the first and second bores extend perpendicular to one another and constitute a part of a valve path, the valve path is open from the control input via the first and second bores to the first connection bore when a sliding valve unit is open.

* * * * *